United States Patent
Seo

(10) Patent No.: US 9,060,796 B2
(45) Date of Patent: Jun. 23, 2015

(54) SURGICAL ROBOT SYSTEM AND CONTROL METHOD THEREOF

(71) Applicant: Samsung Electronics Co., Ltd., Suwon-Si, Gyeonggi-Do (KR)

(72) Inventor: Kee Hong Seo, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 0 days.

(21) Appl. No.: 14/191,945

(22) Filed: Feb. 27, 2014

(65) Prior Publication Data

US 2015/0018841 A1    Jan. 15, 2015

(30) Foreign Application Priority Data

Jul. 10, 2013  (KR) .................. 10-2013-0080809

(51) Int. Cl.
  *A61B 19/00*   (2006.01)
  *A61B 18/00*   (2006.01)
  *B25J 3/00*    (2006.01)

(52) U.S. Cl.
  CPC ............ *A61B 19/2203* (2013.01); *A61B 19/56* (2013.01)

(58) Field of Classification Search
  USPC .............. 700/245, 257, 247, 260; 606/130; 901/8, 6, 2, 28, 41; 600/102, 103
  See application file for complete search history.

(56) References Cited

U.S. PATENT DOCUMENTS

| | | | |
|---|---|---|---|
| 7,996,110 B2 * | 8/2011 | Lipow et al. .................. | 700/245 |
| 2003/0195661 A1 | 10/2003 | Wang et al. | |
| 2007/0013336 A1 * | 1/2007 | Nowlin et al. ........... | 318/568.21 |
| 2011/0319815 A1 * | 12/2011 | Roelle et al. ............... | 604/95.01 |
| 2012/0071752 A1 * | 3/2012 | Sewell et al. .................. | 600/424 |
| 2012/0245595 A1 * | 9/2012 | Kesavadas et al. ........... | 606/130 |
| 2014/0058406 A1 * | 2/2014 | Tsekos ........................... | 606/130 |
| 2014/0142592 A1 * | 5/2014 | Moon et al. ................... | 606/130 |
| 2014/0156074 A1 * | 6/2014 | Seo et al. ....................... | 700/257 |
| 2014/0222023 A1 * | 8/2014 | Kim et al. ..................... | 606/130 |

* cited by examiner

*Primary Examiner* — Ronnie Mnacho
(74) *Attorney, Agent, or Firm* — Harness, Dickey & Pierce, P.L.C.

(57) ABSTRACT

A surgical robot system may include a slave device provided with surgical tools and a master device remotely controlling motion of the surgical tools. The master device may include handles controlling the motion of the surgical tools, a master external force estimator estimating external force applied to the handles, a force compensator generating a first force control signal to cancel out the estimated external force, and a master controller moving and rotating respective joints of the handles in such a way that the external force applied to the handles is canceled out using the generated force control signal.

19 Claims, 11 Drawing Sheets

SURGICAL ROBOT SYSTEM AND CONTROL METHOD THEREOF

CROSS-REFERENCE TO RELATED APPLICATION

This application claims the benefit of Korean Patent Application No. 10-2013-0080809, filed on Jul. 10, 2013 in the Korean Intellectual Property Office, the disclosure of which is incorporated herein by reference.

BACKGROUND

1. Field

Example embodiments relate to a surgical robot system and a control method thereof which may transmit external force applied to surgical tools to an operator without a sensor.

2. Description of the Related Art

Minimally invasive surgery may minimize the size of a surgical incision. In contrast, open surgery may be performed through a large surgical window formed through a portion (for example, the abdomen) of a human body. Minimally invasive surgery may be conducted by observing an image after an endoscope and various surgical tools are inserted into a human body through at least one surgical hole (or invasive hole) having a size of 0.5~1.5 cm formed in the human body.

Such minimally invasive surgery causes relatively less pain after surgery, allows a patient to more rapidly recover intestinal function and resume consumption of solid food, reduces hospital stay, allows the patient to rapidly return to a normal state, and has better aesthetics due to a narrow incisive range, in comparison to open surgery. Due to these advantages, minimally invasive surgery has been used in cholecystectomy, prostate cancer surgery, herniorrhaphy, etc., and application thereof have begun to increase.

In general, a surgical robot used in minimally invasive surgery includes a master device and a slave device. The master device generates a control signal according to operation of a surgeon and transmits the generated control signal to the slave device. The slave device receives the control signal from the master device and provides necessary operation required to perform surgery upon a patient. Surgery may be performed under the condition that the master device and the slave device are integrated or separately provided in an operating room.

The slave device is provided with at least one robot arm, and a surgical instrument is mounted at the end of each robot arm. Here, a surgical tool is mounted at the end of the surgical instrument.

In such minimally invasive surgery using the surgical robot, necessary surgery is performed by inserting the surgical tools and the surgical instruments with the surgical tools of the slave device into the body of a patient. After insertion of the surgical tools and the surgical instruments into the body of the patient, the internal state of the body of the patient is confirmed using an image collected through an endoscope, which is one of the surgical tools.

Further, in the above minimally invasive surgery using the surgical robot, the slave device is located adjacent to the patient and the master device remotely controls operation of the slave device. During surgery through such remote control, it may be desirable to transmit a feedback of the force applied between human tissues of a surgical site and the surgical tool of the slave device to an operator of the master device so that the operator may sense the force applied by the surgical tool.

SUMMARY

Therefore, example embodiments provide a surgical robot system and a control method thereof which may estimate external force applied to surgical tools by detecting movement of a master device and then feed the estimated external force back to the master device.

Additional aspects of the example embodiments will be set forth in part in the description which follows and, in part, will be obvious from the description, or may be learned by practice of the example embodiments.

In accordance with one example embodiments, in a surgical robot system having a slave device provided with surgical tools and a master device remotely controlling motion of the surgical tools, the master device includes handles controlling the motion of the surgical tools, a master external force estimation unit estimating external force applied to the handles, a force compensation unit generating a first force control signal to cancel out the estimated external force, and a master controller moving and rotating respective joints of the handles so that the handles perform motion to cancel out the external force applied to the handles using the generated first force control signal.

In accordance with another example embodiment, a control method of a surgical robot system includes detecting positions and velocities of respective joints of operated handles, generating target positions and target velocities of surgical tools using the detected positions and velocities of the respective joints of the handles, generating compensation control signals compensating for differences between the target positions and target velocities of the surgical tools and current positions and current velocities of the surgical tools, through comparison therebetween, estimating external force applied to the handles using the generated compensation control signals and the detected positions and velocities of the respective joints of the handles, generating a first force control signal canceling out the external force, and driving the respective joints of the handles so that the handles perform motion canceling out the external force according to the generated first force control signal.

One or more example embodiments, relates to a master device configured to control surgical tools of a slave device.

In at least one embodiment, the master device includes an input unit configured to receive input from an operator, the input indicating a desired target position and velocity of the surgical tools; a drive unit configured to move the input unit; and a controller configured to, receive, via a reception unit, detected forces applied to joints of the surgical tools from the slave device, instruct the drive unit to move the input unit with a feedback force that is commensurate with the detected forces applied to the joints of the surgical tools, estimate the input to the input unit by the operator while the drive unit is providing the feedback force to the input unit, instruct the drive unit to move the input unit with an adjustment force that counteracts the input received while providing the feedback force such that the operator can sense the forces applied to the joints of the surgical tools, and transmit, via a transmission unit, the desired target position and velocity of the surgical tools to the slave device.

In at least one embodiment, the input from the operator is conveyed to the input unit by moving joints included in the input unit, and the controller estimates the input using detection units that are configured to detect a position and velocity of the joints included in the input unit.

In at least one embodiment, the input unit includes mechanical fingers that includes the joints, the mechanical fingers configured to be attached to fingers of the operator, the joints providing the mechanical fingers with a certain degree of freedom (DOF).

In at least one embodiment, the slave device is configured to move the surgical tool based on the desired target position and velocity received from the master device.

In at least one embodiment, the controller is configured to estimate the input to the input unit without using a force sensor.

In at least one embodiment, the controller is configured to scale the input from the operator to generate the desired target position and velocity of the surgical tools.

BRIEF DESCRIPTION OF THE DRAWINGS

These and/or other aspects of the example embodiments will become apparent and more readily appreciated from the following description of the embodiments, taken in conjunction with the accompanying drawings of which.

DETAILED DESCRIPTION

Figure 1:
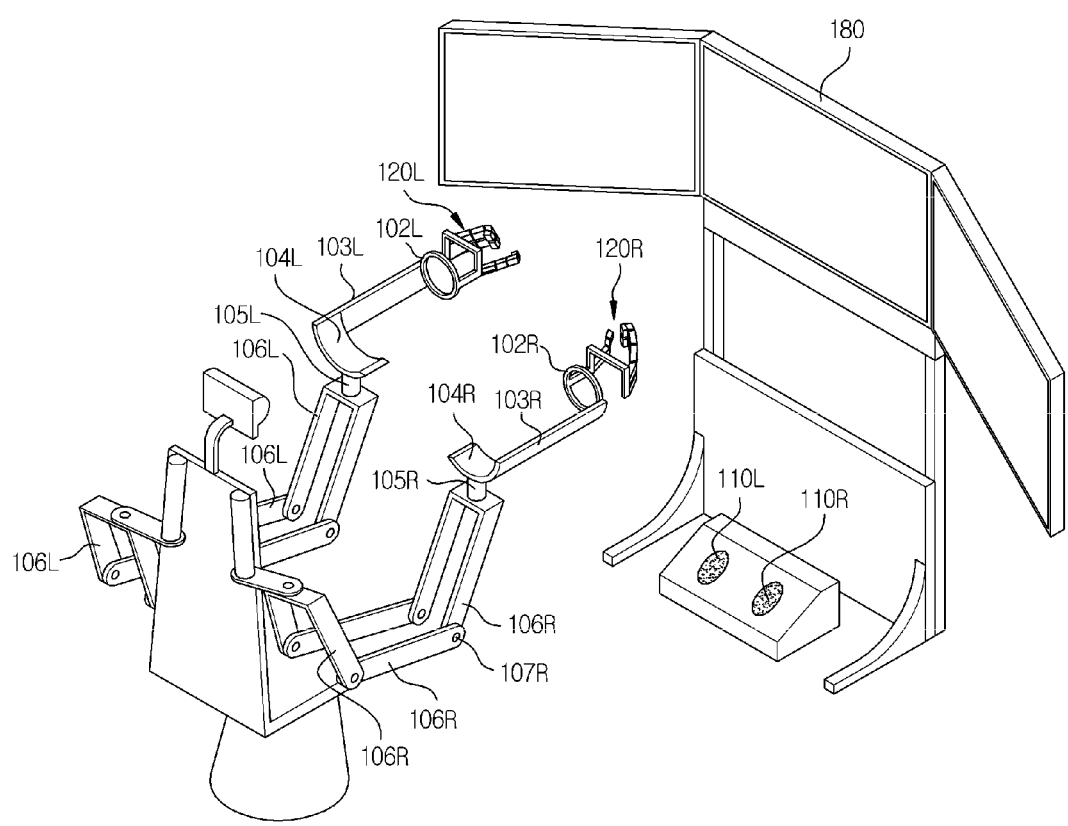
FIG. 1 is a view illustrating the external appearance of a master device of a surgical robot system.

Reference will now be made in detail to embodiments, examples of which are illustrated in the accompanying drawings, wherein like reference numerals refer to like elements throughout. In the drawings, the same or similar elements are denoted by the same reference numerals even though they are depicted in different drawings. In the following description of the example embodiments, a detailed description of known functions and configurations incorporated herein will be omitted when it may make the subject matter of the example embodiments rather unclear. In addition, terms in the following description, such as first, second, etc., are used to discriminate one element from other elements, but do not limit such elements.

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, example embodiments will be described with reference to the accompanying drawings.

In the following description, a single port surgical robot (hereinafter, referred to as a 'surgical robot system') will be exemplarily described, but example embodiments are not limited thereto. For example, embodiments may be applied to various industrial service robot system fields, such as a multi-port surgical robot system, a remote robot system performing various operations in the aerospace industry, a hazardous materials handling robot system through remote control, a pipe cleaning robot system, etc.

FIG. 1 is a view illustrating the external appearance of the master device of a surgical robot system.

Figure 2:
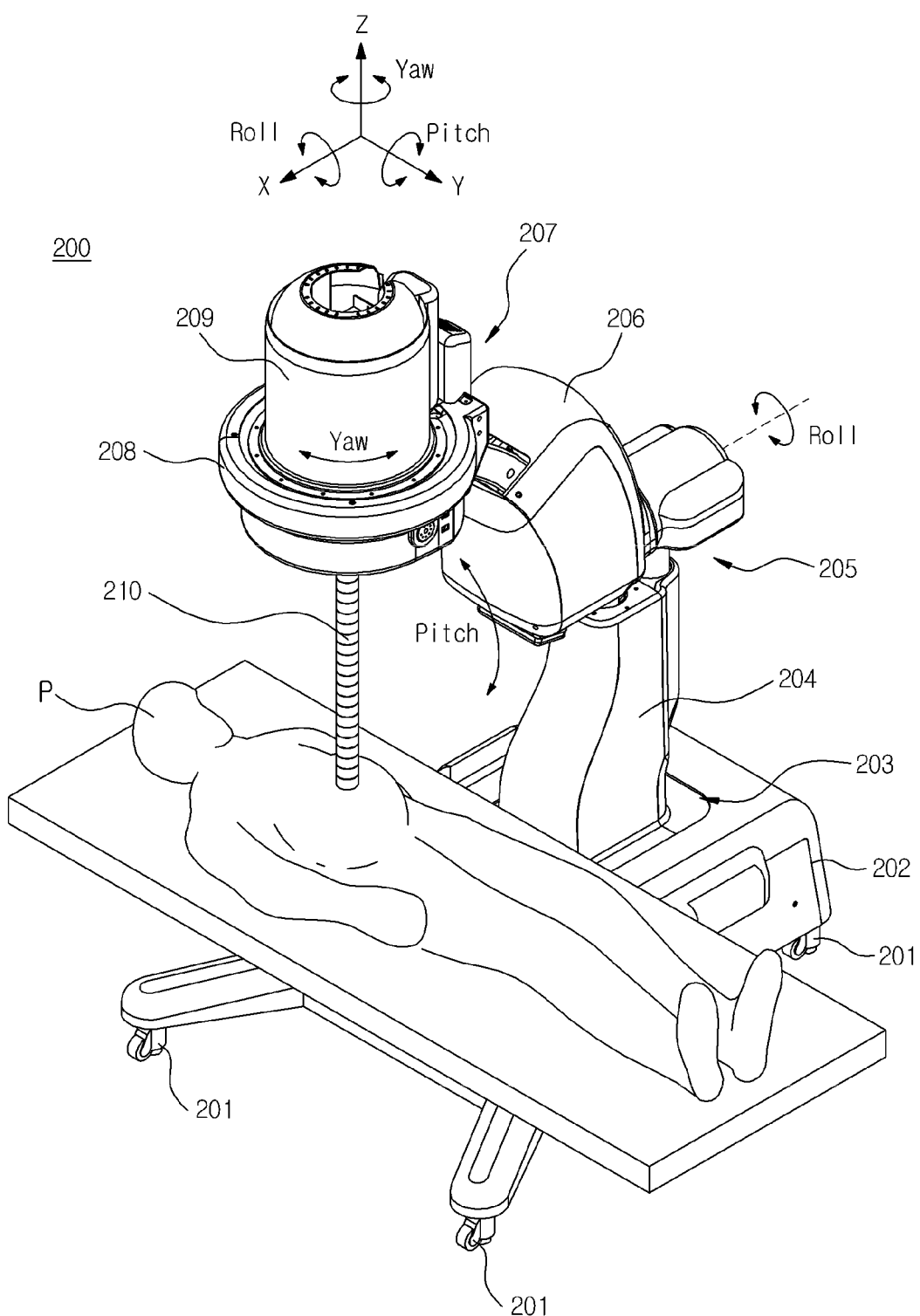
FIG. 2 is a view illustrating the external appearance of a slave device of the surgical robot system.

With reference to FIG. 1, a surgical robot system includes a master device 100 and a slave device 200 illustrated in FIGS. 1 and 2, respectively. The master device 100 remotely controls the slave device 200 (discussed below with reference to FIG. 2). The master device 100 generates a control signal according to operation of an operator, and transmits the generated control signal to the slave device 200. The slave device 200 receives the control signal from the master device 100, and is operated according to the received control signal.

The master device 100 may include an input unit 110L, 110R, 120L, and 120R, and a display unit 180.

The input unit 110L, 110R, 120L, and 120R receives instructions to remotely operate the slave device 200 (with reference to FIG. 2) from an operator (for example, a surgeon). The input unit 110L, 110R, 120L, and 120R may include two clutch pedals 110L and 110R and two handles 120L and 120R, however, the input unit 110L, 110R, 120L, and 120R is not limited thereto and may further include a switch, a button, a voice recognition device, etc.

The clutch pedals 110L and 110R may be used to convert between operation modes of the surgical robot system. For example, if the left clutch pedal 110L is operated, a guide tube operation mode may be performed. Likewise, if the right clutch pedal 110R is operated, a surgical instrument operation mode may be performed. When the guide tube operation mode is performed, the operator may change the position and pose of a guide tube 210 (with reference to FIG. 2) by operating the handles 120L and 120R. Further, when the surgical instrument operation mode is performed, the operator may change the positions, poses, and operations of surgical tools 212 and 214 (with reference to FIG. 3), attached to the guide tube 210, by operating the handles 120L and 120R.

Further, the handles 120L and 120R may control movement of a robot arm 203-208, the guide tube 210, the surgical tools 212 and 214 and an endoscope 216 provided on the slave device 200 (with reference to FIG. 2). The handles 120L and 120R may be implemented as haptic devices, but are not limited thereto. Further, the handles 120L and 120R may include one or more multi-joint robot fingers. The multi-joint robot fingers may be disposed in a shape similar to that of a human hand. FIG. 1 illustrates that three multi-joint robot fingers are provided at positions corresponding to the thumb, the forefinger, and the middle finger of a human hand, however, the number and positions of the multi-joint robot fingers are not limited thereto.

Further, each of the multi-joint robot fingers may include plural links and plural joints. A 'joint' may mean a connection region between a link were a link may have at least 1 degree of freedom (DOF) in forward kinematics or inverse kinematics. The DOF being the number of independent movements of relative positions of respective links. For example, an object in 3D space formed by an X-axis, a Y-axis, and a Z-axis has at least a DOF of "1" from among 3 DOFs to determine the spatial position of the object (positions of the object on the respective axes) and 3 DOFs to determine the spatial orientation of the object (rotation angles of the object about the respective axes). In more detail, it may be understood that, if the object is movable along the respective axes and is rotatable about the respective axes, the object has a DOF of "6". The state of the joints of the multi-joint robot fingers may be detected by detection units, for example, a position (e.g., a joint angle) and velocity of the joints may be detected by a position detection unit 122 and a velocity detection unit 124 (with reference to FIG. 4), respectively.

Further, an annular insertion hole, into which the tip of a finger of the operator is inserted, may be provided at each of the front ends of the multi-joint robot fingers. Therefore, movement of the multi-joint robot fingers may correspond to movement of the fingers of the operator when the operator's fingers are inserted into the insertion holes. The detection units provided at the respective joints of the multi-joint robot fingers may detect information regarding the states of the moving joints.

The positions and velocities of the respective joints detected through the position detection units 122 and the velocity detection units 124 may be converted into control signals regarding target positions and target velocities which the respective joints of the surgical tools 212 and 214 of the slave device 200 should follow, and the control signals may be transmitted to the slave device 200 through a network. The network may be a wired network, a wireless network, or a wired/wireless hybrid network.

The handles 120L and 120R shown in FIG. 1 are in the shape of a hand, however, the handles 120L and 120R may have a pencil shape, a stick shape, or the shape of a surgical tool. Further, although FIG. 1 illustrates the left handle 120L and the right handle 120R as having the same shape, the left handle 120L and the right handle 120R are not limited thereto and may have different shapes.

Support links 103L and 103R that are mechanically connected to the respective handles 120L and 120R may be provided to support the arms of the operator from wrists to elbows. The support links 103L and 103R may include wrist support parts 102L and 102R and elbow support parts 104L and 104R.

The wrist support parts 102L and 102R may be arranged at positions corresponding to the wrists of the operator and have various shapes. For example, as illustrated in FIG. 1, the wrist support parts 102L and 102R may have an annular shape. The operator may put the hands into the wrist support parts 102L and 102R and, then, insert the tips of the fingers into the insertion holes provided at the front ends of the handles 120L and 120R.

The elbow support parts 104L and 104R may be arranged at positions corresponding to the elbows of the operator. As illustrated in FIG. 1, the elbow support parts 104L and 104R may have a U-shape, but are not limited thereto.

The support links 103L and 103R including the wrist support parts 102L and 102R and the elbow support parts 104L and 104R may keep the arms of the operator in a stable state, thus allowing the operator to stably operate the master device 100.

Further, at least one connection link 106L or 106R mechanically connecting each of the support links 103L and 103R to a chair upon which the operator sits may be provided. Joints 105L and 105R may be provided between the connection links 106L and 106R and the support links 103L and 103R. Further, plural connection links 106L and 106R may be provided with joints 107L and 107R, respectively connecting the plural connection links 106L and 106R to the support links 103L and 103R.

Although FIG. 1 illustrates the two handles 120L and 120R as being mechanically connected to the chair by the support links 103L and 103R and the connection links 106L and 106R, the structure of the master device 100 is not limited thereto. For example, the support links 103L and 103R and the connection links 106L and 106R may be omitted, and, instead each of the handles 120L and 120R may further include a communication unit (not shown) to transmit and receive data through wired communication or wireless communication with a controller (not shown) of the master device 100.

The display unit 180 may include one or more monitors such that information necessary during surgery may be displayed through the respective monitors. As one example, if the display unit 180 includes three monitors, as shown in FIG. 1, one monitor may display a real image collected through the endoscope 217 (with reference to FIG. 2) and a virtual 3D image converted from a medical image of the patient captured prior to surgery. The two other monitors may respectively display information regarding the operating state of the slave device 200 and patient information. As another example, the plural monitors may display the same image. In this case, the same image may be displayed through the respective monitors, or one image may be displayed through the entirety of the plural monitors. The number of monitors may be variously determined according to types and kinds of information to be displayed. The above-described display unit 180 may include a liquid crystal display (LCD), a light emitting diode (LED), an organic light emitting diode (OLED), a plasma display panel (PDP), or a combination thereof, but is not limited thereto.

Here, "patient information" may be information indicating the state of the patient, for example, biometric information, such as body temperature, pulse, respiration, and blood pressure. In order to provide such biometric information to the master device 100, the slave device 200, which will be described later, may further include a biometric information measurement unit including a body temperature measurement module, a pulse measurement module, a respiration measurement module, and a blood pressure measurement module. For this purpose, the master device 100 may further include a signal processing unit (not shown) to receive and process the biometric information transmitted from the slave device 200 and to output the processed biometric information to the display unit 180.

FIG. 2 is a perspective view illustrating the external appearance of the slave device 200.

With reference to FIG. 2, the slave device 200 may include a caster unit 201, a body 202, a robot arm 203~208, and a surgical tool assembly 209.

The caster unit 201 serves to move the slave device 200, and may be mounted at the lower part of the body 202. The caster unit 201 may include plural casters. Each of the casters may include a lever (not shown) to change the operating state of the caster. The operator may change the operating states of the casters by adjusting the positions of the levers (not shown). The operating states of the casters may include a brake state, a free swivel state, and a directional lock (or swivel lock) state.

The robot arm 203~208 may be provided at the upper part of the body 202. The robot arm 203~208 may move the surgical instrument assembly 209 along at least one of a x-axis, a y-axis, and a z-axis, or rotate the surgical instrument assembly 209 about at least one of the x-axis, the y-axis, and the z-axis. Further, the robot arm 203~208 may support the surgical tool assembly 209 so that the position and pose of the surgical tool assembly 209 may be maintained during surgery.

The robot arm 203~208 may include plural link units 204, 206, and 208, and plural joint units 203, 205, and 207. In more detail, the robot arm 203~208 may include a first joint unit 203, a first link unit 204, a second joint unit 205, a second link unit 206, a third joint unit 207, and a third link unit 208.

The first link unit 204 may include a first link and a casing surrounding the first link. The first link may have a rectilinear column shape and be provided in the direction perpendicular to the body 202 and the ground.

The first joint unit 203 is provided at the connection region between the body 202 and the first link unit 204, and may include a prismatic joint moving along a designated axis among the x-axis, the y-axis, and the z-axis. The first joint unit 203 serves to perform linear motion of the surgical instrument assembly 209, and may have 3 DOF but is not limited thereto. For this purpose, the first joint unit 203 may include a linear drive unit, and the linear drive unit may include a linear motion guide guiding linear motion along a specific axis and a motor providing driving force to the linear motion guide.

The second link unit 206 may be arranged at the end of the first link unit 204 and include a second link and a casing surrounding the second link. As shown in FIG. 2, the second link may have a curved shape, but example embodiments are not limited thereto.

The second joint unit 205 is provided at the connection region between the first link unit 204 and the second link unit 206, and may include a revolute joint rotating about a designated axis among the x-axis, the y-axis, and the z-axis. The second joint unit 205 serves to perform rotary motion of the surgical tool assembly 209, and may have 2 DOF but is not limited thereto. The 2 DOF of the second joint unit 205 may include rotation in the roll direction and rotation in the pitch direction, but is not limited thereto. For this purpose, the second joint unit 205 may include a roll drive unit and a pitch drive unit. The roll drive unit and the pitch drive unit may be one of a motor, a vacuum pump, and a hydraulic pump, but are not limited thereto.

As shown in FIG. 2, the third link unit 208 may be arranged at the end of the second link unit 206 and include an annular third link. The surgical tool assembly 209 may be arranged on the annular third link.

The third joint unit 207 is provided at the connection region between the second link unit 206 and the third link unit 208, and may include a revolute joint rotating about a designated axis among the x-axis, the y-axis, and the z-axis. The third joint unit 207 serves to perform rotary motion of the surgical instrument assembly 209, and may have 1 DOF but is not limited thereto. In more detail, the 1 DOF of third joint unit 207 may include rotation in the yaw direction, but is not limited thereto. For this purpose, the third joint unit 207 may include a yaw drive unit. The yaw drive unit may be one of a motor, a vacuum pump, and a hydraulic pump, but is not limited thereto.

The surgical tool assembly 209 may include a cylindrical casing, the plural surgical tools 212 and 214 provided along the inner surface of the casing, the endoscope 216, and the guide tube 210. Further, the surgical tool assembly 209 may include a base station (not shown) to which the surgical tools 212 and 214, the endoscope 216, and the guide tube 210 are fixed, but is not limited thereto. Among the plural surgical tools 212 and 214 provided along the inner surface of the casing, at least one surgical tool selected by the operator may enter the abdominal cavity of a patient through the guide tube 210.

The surgical tool assembly 209 may be mechanically separated from the third link unit 208. If the surgical tool assembly 209 is separated from the third link unit 208, it may be easier to replace a surgical tool or to disinfect a surgical tool used in surgery.

Figure 3:
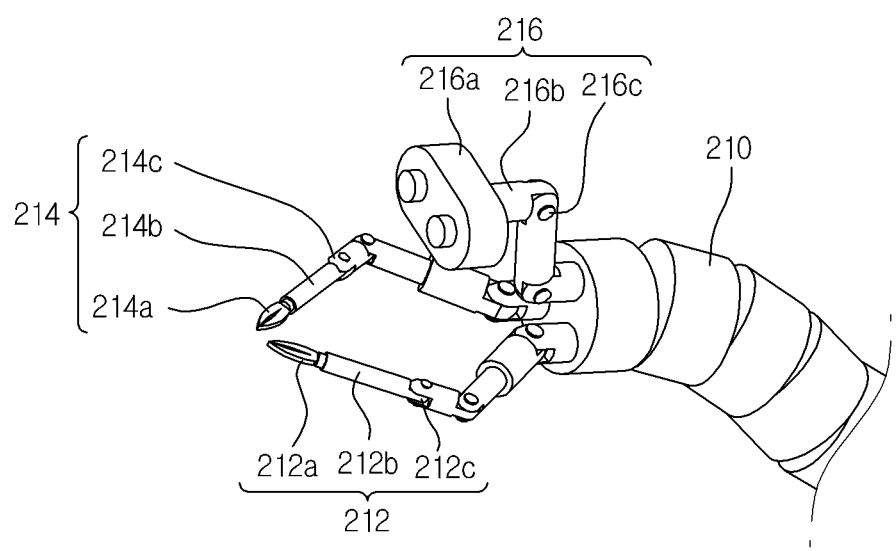
FIG. 3 is a view illustrating surgical tools spread through a guide tube.

FIG. 3 is a view illustrating the surgical tools spread through the guide tube.

As illustrated in FIG. 3, at least one of the surgical tools 212 and 214 may enter into the abdominal cavity of a patient along the guide tube 210. Entry of the surgical tools 212 and 214 into the abdominal cavity of the patient through the guide tube 210 may be performed through various methods. The guide tube 210 may first enter into the abdominal cavity of the patient and move to a target position, e.g., a surgical site, and then movement of the guide tube 210 may be fixed. Next, the surgical tools 212 and 214 may be inserted into a passage provided within the guide tube 210, move along the passage, and enter into the abdominal cavity of the patient. The endoscope 216 may be inserted into the guide tube 210 before the guide tube 210 is inserted into the abdominal cavity of the patient such that the guide tube 210 can be moved to the surgical site while observing an image of the inside of the abdominal cavity after insertion of the guide tube 210 into the abdominal cavity of the patient.

The guide tube 210 may enter into the abdominal cavity of a patient and moved to the surgical site. Thereafter, as illustrated in FIG. 3, the movement of the guide tube 210 may be fixed and the surgical tools 212 and 214 may be spread to the outside of the guide tube 210 so as to reach the surgical site.

With reference to FIG. 3, the two surgical tools 212 and 214 and the endoscope 216 may include a plurality of links 212b, 214b, and 216b, a plurality of joints 212c, 214c, and 216c, and end effectors 212a, 214a, and 216a mounted at the tips of the links 212b, 214b, and 216b, but are not limited thereto.

Each of the joints 212c, 214c, and 216c may be one of a fixed joint, a revolute joint rotating about a designated axis among the x-axis, the y-axis, and the z-axis, and a prismatic joint linearly moving along a designated axis among the x-axis, the y-axis, and the z-axis, and have 1 or more DOF.

A drive unit 270 (with reference to FIG. 4) may be provided at each of the joints 212c, 214c, and 216c. The drive unit 270 is driven according to a motion control signal received from the master device 100 to move the corresponding joint. The drive unit 270 may be one of a motor, a vacuum pump, and a hydraulic pump, but is not limited thereto. Hereinafter, the case that a motor is used as the drive unit 270 will be exemplarily described.

Further, a detection unit may be provided at each of the joints 212c, 214c, and 216c. The detection unit may include a position detection unit 222 (with reference to FIG. 4) to detect the position of each joint (e.g., a joint angle), and a velocity detection unit 224 (with reference to FIG. 4) to detect the velocity of each joint.

Hereinafter, the configuration of the surgical robot system according to one or more example embodiment will be described in detail, with reference to FIG. 4.

Figure 4:
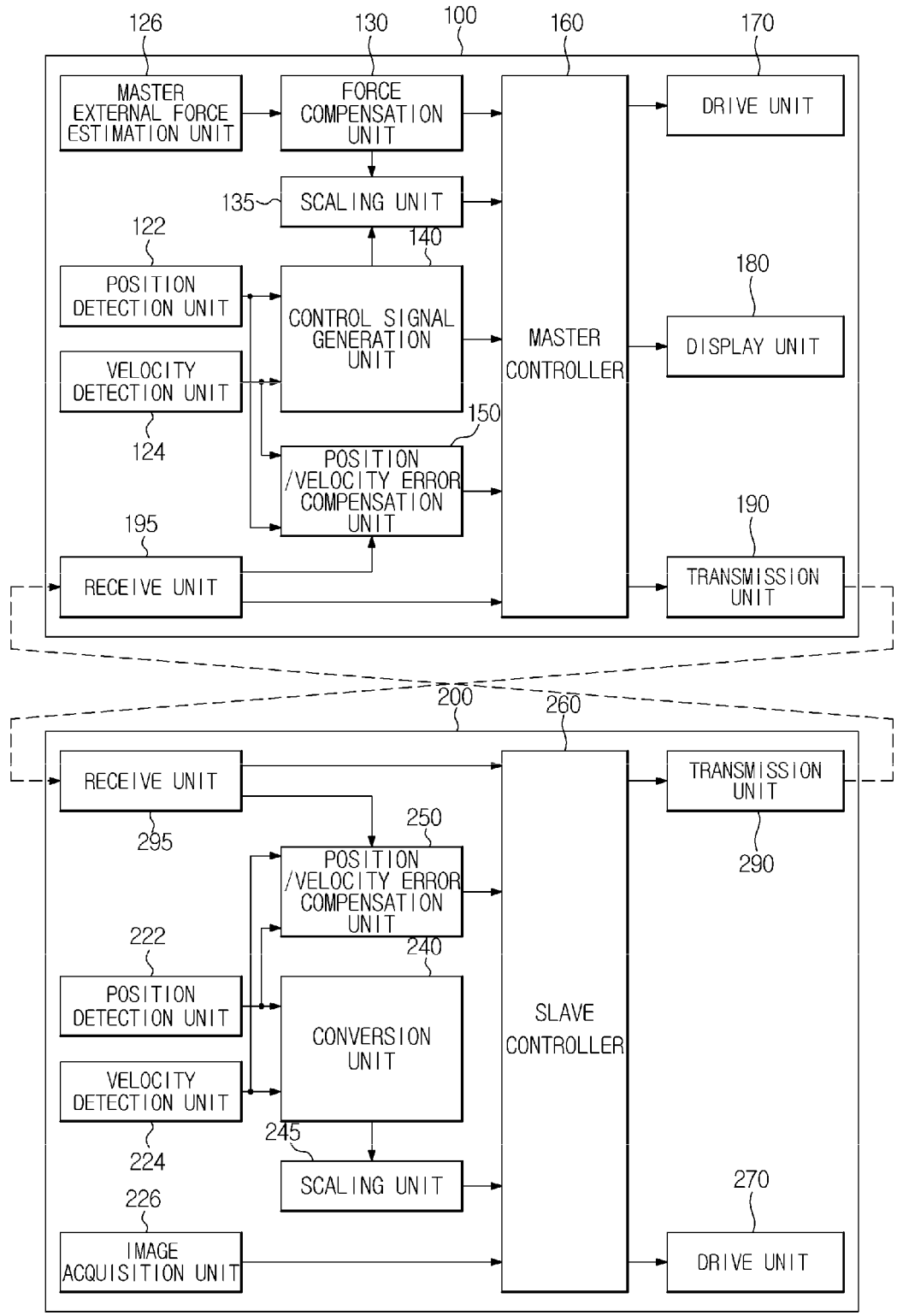
FIG. 4 is a block diagram illustrating one example of the configuration of the surgical robot system.

FIG. 4 is a block diagram illustrating a configuration of a surgical robot system according to an example embodiment.

With reference to FIG. 4, the master device 100 of the surgical robot system may include a master external force estimation unit 126, position detection units 122, velocity detection units 124, a force compensation unit 130, a scaling unit 135, a control signal generation unit 140, a position/velocity error compensation unit 150, a master controller 160, drive units 170, the display unit 180, a transmission unit 190, and a receive unit 195.

The master external force estimation unit 126 estimates external force applied to the handles 120L and 120R of the input unit 110L, 110R, 120L, and 120R of the master device 100. The external force may be applied to the handles 120L and 120R by operation of an operator. The external force estimated by the master external force estimation unit 126 may be provided to the force compensation unit 130 which will be described later.

The master external force estimation unit 126 may apply a Kalman filter to a motion equation model of the handles 120L and 120R, and estimate external force applied to the handles 120L and 120R using force output from the master controller 160 according to the positions and velocities of the respective joints of the handles 120L and 120R and first compensation control signals. The positions and velocities of the joints of the handles 120L and 120R may be detected through the position detection units 122 and the velocity detection units 124, respectively, and the first compensation control signals may be generated through the position/velocity error compensation unit 150.

Equation 1 below represents a motion equation model of the handles 120L and 120R.

$$M_m \ddot{x}_m = F_h - \gamma \hat{F}_h + [k_p(x_s - x_m) + k_v(v_s - v_m)] \quad \text{(Equation 1)}$$

In equation 1, subscript m denotes relation with the handles of the master device, subscript s denotes relation with the surgical tools of the slave device, M represents a mass, F represents force, x represents displacement, v represents velocity, $\ddot{x}$ represents acceleration, $k_p$ represents position error compensation gain, and $k_v$ represents velocity error compensation gain. Further, $F_h$ represents actual force applied to the handles by an operator, $\hat{F}_h$ represents an estimated value of the force applied to the handles by the operator, and $\gamma$ represents proportional gain.

The external force applied to the handles 120L and 120R by the operator may be estimated by applying the Kalman filter to the model of the handles 120L and 120R, as stated in Equation 1. First, as stated in Equation 2 below, the position p, velocity v, and external force f of each DOF of translation motion in the x-axis, y-axis, and z-axis directions are set as a state vector w of the Kalman filter.

$$w = \begin{pmatrix} p \\ v \\ f \end{pmatrix} \quad \text{(Equation 2)}$$

According to general formulation of the Kalman filter, a state at the next sampling time, e.g., position, velocity, and external force at the next sampling time, is predicted. Equation 3 below represents a model used at this time.

$$w' \leftarrow Fw + Bu$$

$$P \leftarrow FPF^T + Q \quad \text{(Equation 3)}$$

In equation 3, w' represents predicted values of position, velocity, and external force at the next sampling time. Further, u represents a system input, e.g., force (torque) determined by the master controller 160 and output to the handles 120L and 120R, actually represents internal force driving the corresponding DOF, and may be expressed as $f_c$. P represents covariance of the state vector w, is converged upon a small value during a filtering process, and may be used as a criterion representing uncertainty of the estimated state vector w.

Further, F, B, and Q are stated as in Equations 4, 5, and 6 below.

$$F = \begin{pmatrix} 1 dt & -\dfrac{dt^2}{2M_m} \\ & 1 & -\dfrac{dt}{M_m} \\ & & 1 \end{pmatrix} \quad \text{(Equation 4)}$$

$$B = \begin{pmatrix} \dfrac{dt^2}{2M_m} \\ \dfrac{dt}{M_m} \\ 0 \end{pmatrix} \quad \text{(Equation 5)}$$

$$Q = GG^T \quad \text{(Equation 6)}$$

-continued where $$G = \begin{pmatrix} \frac{dt^2}{2M_m}\sigma_F \\ \frac{dt}{M_m}\sigma_F \\ dt\sigma_{Fe} \end{pmatrix} \quad \text{(Equation 7)}$$

In equations 4-7, dt represents a sampling period, $\sigma_F$ represents a standard deviation representing a level of an error of a motion model of a mass $M_m$ due to the sum ($f_c-f$) of internal force and external force, and $\sigma_{Fe}$ represents a standard deviation of change probability distribution of external force f.

Based on such a model, an object having a mass $M_m$ may be accelerated by the sum of internal force and external force, e.g., $f_c-f$, and the next velocity and next position may be predicted by such acceleration.

Further, it may be assumed that external force f may be arbitrarily changed from force f at the earlier sampling time according to a normal distribution regardless of input and other states.

After the above-described prediction process, the predicted positions and velocities of the handles 120L and 120R are corrected using actually measured values of the positions and velocities of the handles 120L and 120R, detected by the position detection units 122 and the velocity detection units 124. A method of correcting the predicted values using the actually measured values is as follows.

First, a measurement error vector e is calculated using the measured values. In this embodiment, the measurement error vector e may be calculated using Equation 8 below.

$$e = H(z - w') \quad \text{(Equation 8)}$$

In equation 8, z is a vector of measured values of the position and velocity of the handles 120L and 120R, and may be expressed as ($p_m$ $v_m$ 0). Since there is no measure of the external force applied to the handles 120L and 120R, the third component of z becomes 0. Here, $p_m$ and $v_m$ are measured position and measured velocity, and an observation model H is as in Equation 9 below.

$$H = \begin{pmatrix} 1 & 0 & 0 \\ 0 & 1 & 0 \end{pmatrix} \quad \text{(Equation 9)}$$

Further, Kalman gain K is calculated through Equations 10, 11, and 12 below. First, innovation covariance S is calculated using Equation 10 below.

$$S = HPH^T + R \quad \text{(Equation 10)}$$

In equation 10, R represents covariance when measured values are represented as a normal distribution, and may be defined as Equation 11 below.

$$R = H \sum^T \sum H^T \quad \text{(Equation 11)}$$

$$\sum = \begin{pmatrix} \sigma_p & & \\ & \sigma_v & \\ & & 0 \end{pmatrix}$$

In equation 11, $\sigma_p$ represents a standard deviation of the measured position value, and $\sigma_v$ represents a standard deviation of the measured velocity value.

Using the values of H, S and P, the Kalman gain K may be calculated as Equation 12 below.

$$K = PH^T S^{-1} \quad \text{(Equation 12)}$$

A predicted value w' and a matrix representing covariance of the state vector are corrected using the Kalman gain K, calculated, as stated in Equation 13 below, using above Equations 10, 11, and 12, and the measurement error vector e, calculated using above Equation 8. Here, the third component f of the corrected predicted value w corresponds to an estimated value of the external force applied to the handles 120L and 120R by operation of the operator.

$$w \leftarrow w' + Ke$$

$$P \leftarrow (1 - KH)P \quad \text{(Equation 13)}$$

The force compensation unit 130 may generate a control signal to cancel out force, applied to the handles 120L and 120R by the operator, by multiplying the external force, estimated through the master external force estimation unit 126, by negative gain ($-\gamma$). Further, the force compensation unit 130 may generate a control signal to operate the surgical tools 212 and 214 of the slave device 200 so as to follow force applied to the handles 120L and 120R by multiplying the external force, estimated through the master external force estimation unit 126, by positive gain.

Hereinafter, the force control signal acquired by multiplying the external force by the negative gain will be referred to as a first force control signal, and the force control signal acquired by multiplying the external force by the positive gain will be referred to as a second force control signal. The force compensation unit 130 may provide the generated first force control signal to the master controller 160 and provide the generated second force control signal to the scaling unit 135.

The absolute values of the negative gain and the positive gain may be equal to each other, or be different from each other.

Further, the gain may have a value which is greater than 0 and less than 1, but is not limited thereto. However, in order to assure stability of a system, the value of the gain may be set to a value of less than 1. This will be described using equations, as follows.

A motion equation model of the handles 120L and 120R of the master device 100 and a motion equation model of the surgical tools 212 and 214 of the slave device 200 may be expressed as Equations (14) and Equation (15) below, respectively.

$$M_m \ddot{x}_m = F_h - \gamma \hat{F}_h + [k_p(x_s - x_m) + k_v(v_s - v_m)] \quad \text{(Equation 14)}$$

$$M_s \ddot{x}_s = F_e - \gamma \hat{F}_h + [k_p(x_m - x_s) + k_v(v_m - v_s)] \quad \text{(Equation 15)}$$

In equations 14 and 15, $F_e$ represents force applied to the external environment by the surgical tools 212 and 214. (Since the motion equation model is viewed from the standpoint of the slave device, $-F_e$ means force applied from the external environment to the surgical tools 212 and 214.)

Assuming that performance of the master external force estimation unit 126 is excellent and the estimated external force $\hat{F}_h$ and the force $F_h$ actually applied by the operator are equal, Equations 14 and 15 above may be modified into Equations 16 and 17 below.

$$M_m \ddot{x}_m = (1-\gamma)F_h + [k_p(x_s - x_m) + k_v(v_s - v_m)] \quad \text{(Equation 16)}$$

$$M_s \ddot{x}_s = -F_e + \gamma F_h + [k_p(x_m - x_s) + k_v(v_m - v_s)] \quad \text{(Equation 17)}$$

Further assuming that the handles 120L and 120R and the surgical tools 212 and 214 are in a dynamic equilibrium state, e.g., in a stoppage state in which acceleration z is 0, relations between the force applied to the handles by the operator $F_h$ and the force $F_e$ applied by the surgical tools in such a dynamic equilibrium state may be expressed through equations 18 and 19.

$$(\gamma-1)F_h = k_p(x_2-x_m)+k_v(v_s-v_m) \quad \text{(Equation 18)}$$

$$F_e = \gamma F_h + (1-\gamma)F_h = F_h \quad \text{(Equation 19)}$$

As shown in Equation 19, the force $F_h$ applied to the handles by the operator and the force $F_e$ applied to the external environment by the surgical tools are equal.

The gain γ may be 0 when the external force $F_h$ applied to the handles 120L and 120R by the operator is not measured or estimated, and feedback force is provided only in proportion to errors between the current position and current velocity of the surgical tools 212 and 214 and the positions and velocities of the respective joints of the operated handles 120L and 120R.

When the handles 120L and 120R are not in the dynamic equilibrium state, such that the acceleration is greater than 0, the =force applied to the handles by the operator $F_h$ may be expressed as equation 20 below rather than equation 18.

$$F_h = -\frac{k_p}{1-\gamma}(x_s-x_m) - \frac{k_v}{1-\gamma}(v_s-v_m) \quad \text{(Equation 20)}$$

In equation 20, as γ is closer to 1, stiffness of the system increases, and when γ becomes 1, stiffness of the system become ideally infinite and thus errors between the position and velocity of the handles 120L and 120R and the position and velocity of the surgical tools 212 and 214 become 0. However, since the case that γ is 1 corresponds to a boundary at which the system becomes unstable, γ may have a value of less than 1.

By applying such a value of γ, even if the conventional method, in which feedback force is provided in proportion to errors between the current position and current velocity of the surgical tools 212 and 214 and the positions and velocities of the respective joints of the operated handles 120L and 120R, is used, stiffness of the system may increase and thus, a hard object having stiffness greater than original stiffness may be identified. This identification may be useful in haptic sensing an object in a remote place through feedback force, and in case of a surgical robot, increase an opportunity that elasticity of tissues which a surgical tool contacts may be judged by touch.

As described above, the surgical robot system may not utilize a force sensor installed at the surgical tools 212 and 214 or the handles 120L and 120R to measure external force and thus simplifies the configuration of the surgical robot system, and expands a range of sensible hardness, as compared to the conventional method of providing feedback force only using position and velocity errors between the surgical tools 212 and 214 and the handles 120L and 120R.

Figure 6:
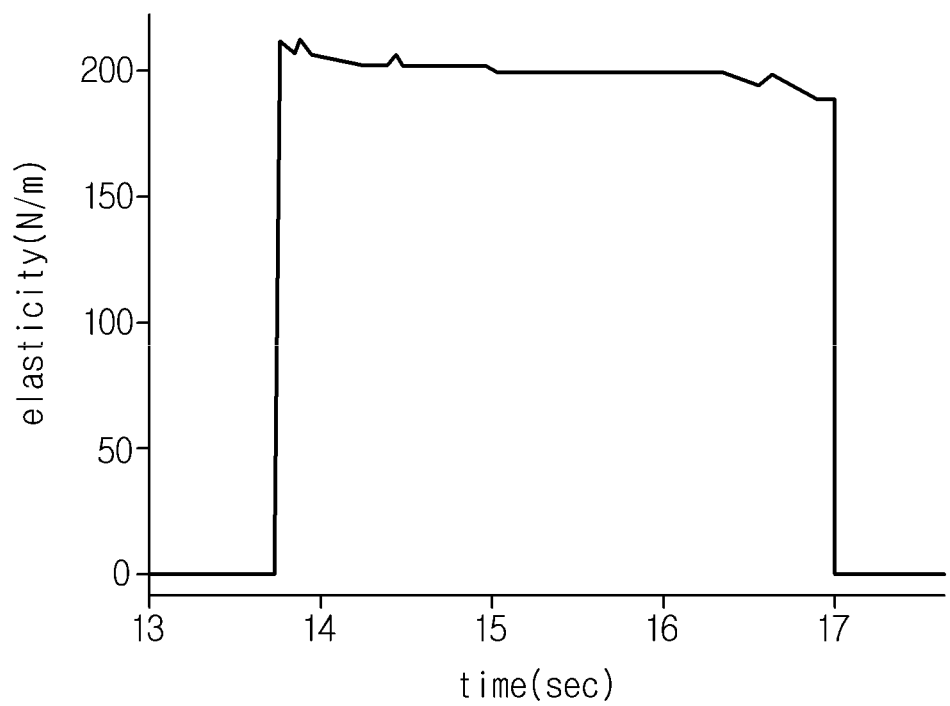
FIG. 6 is a graph representing test results using a conventional method of providing feedback force in proportion to position and velocity errors between a master device and a slave device.
Figure 7:
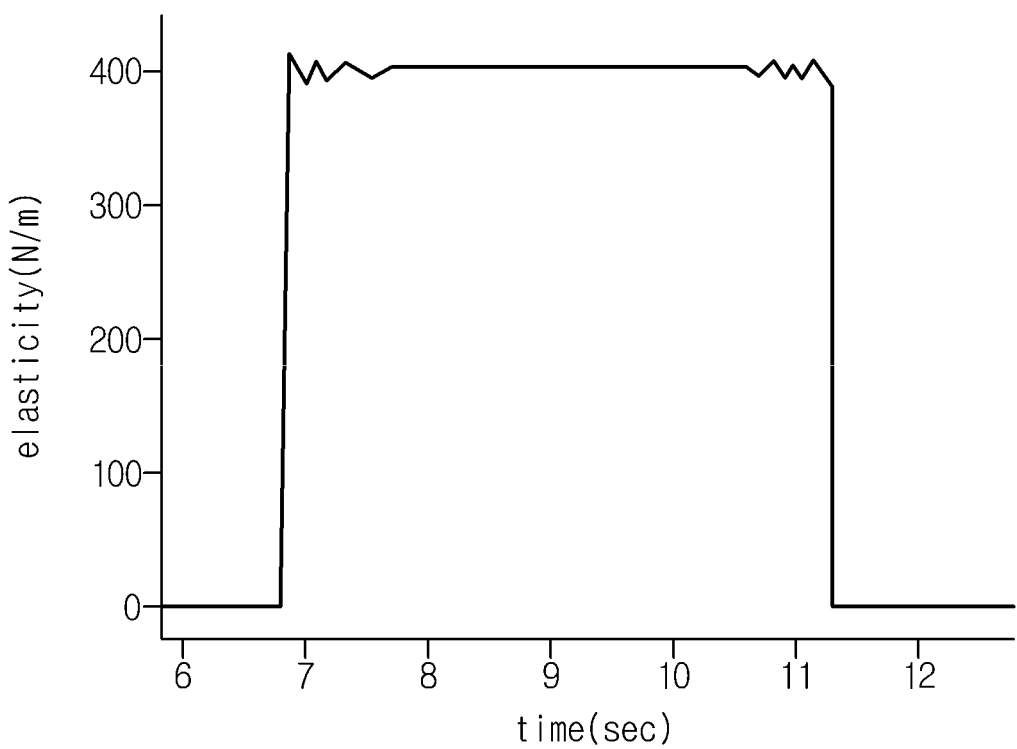
FIG. 7 is a graph representing test results using a conventional method of applying estimated force to force in proportion to position and velocity errors between a master device and a slave device.
Figure 8:
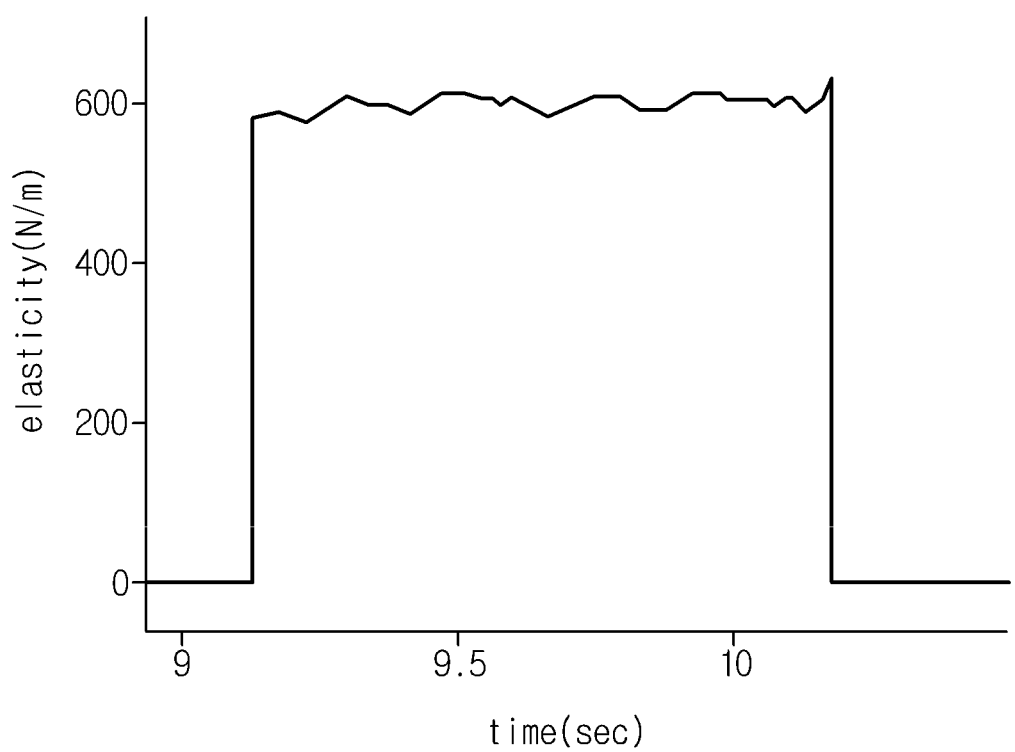
FIG. 8 is a graph representing test results if proportional gain is increased under the condition of FIG. 7.

FIGS. 6, 7 and 8 are graphs representing results of a test performed using a surgical robot system according to an example embodiment. In the test, the Master device includes 2 commercial haptic devices (Omega-7 manufactured by Force Dimension) and the Slave device includes a surgical simulator having a surgical tool attached thereto. A proportional constant between a position error between the master device and the slave device and feedback force felt by an operator corresponds to hardness (elasticity) of a wall contacted by the surgical tool. Since the wall of the simulator is infinitely hard, it may be judged that, as hardness of the wall felt by the user increases, performance becomes excellent.

FIG. 6 is a graph representing elasticity felt by a user, if the conventional method where a position error between the master device and the slave device is used without estimating the force applied to the master device by the user.

As illustrated in FIG. 6, when the position control gain $k_p$ is 200, the measured elasticity is 200 N/m. That is, only elasticity corresponding to the position control gain $k_p$ is transmitted as feedback force. In such a convention case, elasticity is calculated by the intensity of feedback force of the master device to setting of displacement between the master device and the slave device, and corresponds to hardness of a wall set in simulation, felt by an operator operating the master device.

FIG. 7 is a graph representing elasticity felt by the user, if both the estimated value of the force applied to the master device by the user and the position error between the master device and the slave device are used when the proportional gain γ of the estimated value is 0.5. FIG. 8 is a graph representing elasticity felt by the user, if the proportional gain γ of the estimated value is adjusted to 0.67.

In FIGS. 7 and 8, the position control gain $k_p$ is 200.

With reference to FIG. 7, measured elasticity is 400 N/m. In contrast, as discussed above, in FIG. 6, the measured elasticity is 200 N/m. Therefore, when the estimated value of the force applied to the master device by the user is utilized, the user may feel elasticity 2 times the position control gain $k_p$, as compared to FIG. 6. Further, with reference to FIG. 8, the measured elasticity is 600 N/m, and, therefore, the user may feel elasticity 3 times the position control gain $k_p$, as compared to FIG. 6, and feel elasticity 1.5 times, as compared to FIG. 7.

If feedback force to which the estimated value of external force applied to the handles 120L and 120R is provided, as in the test results, elasticity closer to elasticity of an object which the surgical tool actually contacts may be reproduced through the handles 120L and 120R even though the same position control gain and velocity control gain are used, as compared to the conventional method of providing feedback force using only a position error and a velocity error between the master device and the slave device.

Figure 9:
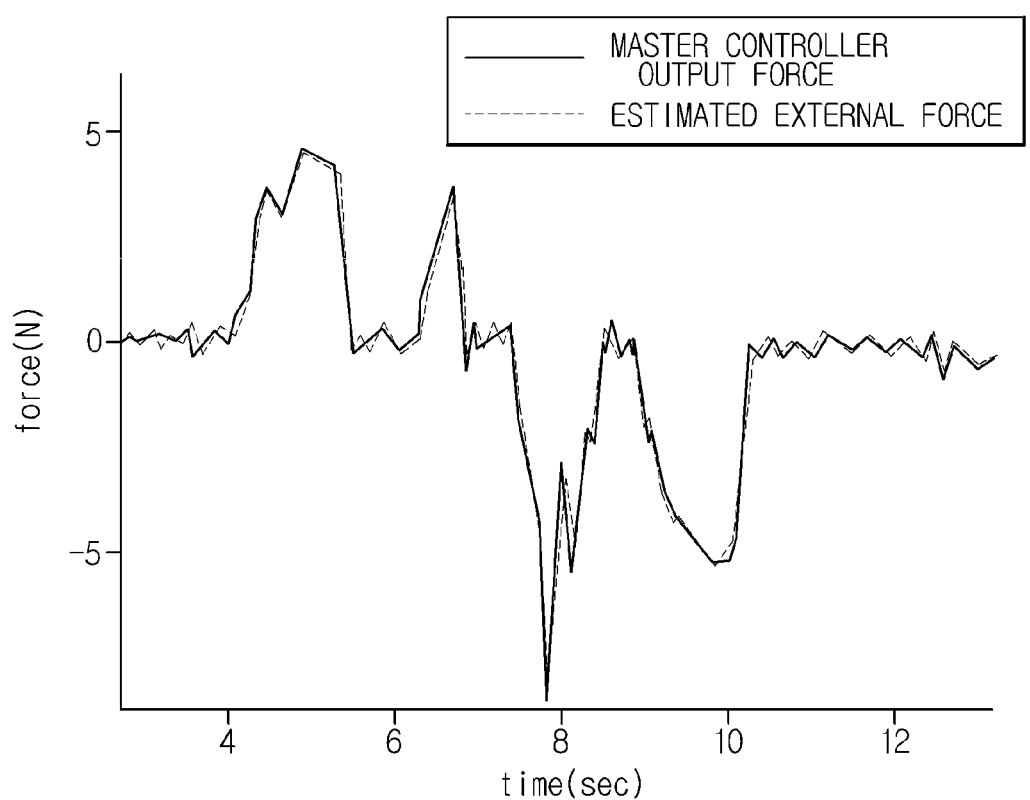
FIG. 9 is a graph representing test results regarding relations between master controller output force to a DOF in the x-axis direction and estimated external force.
Figure 10:
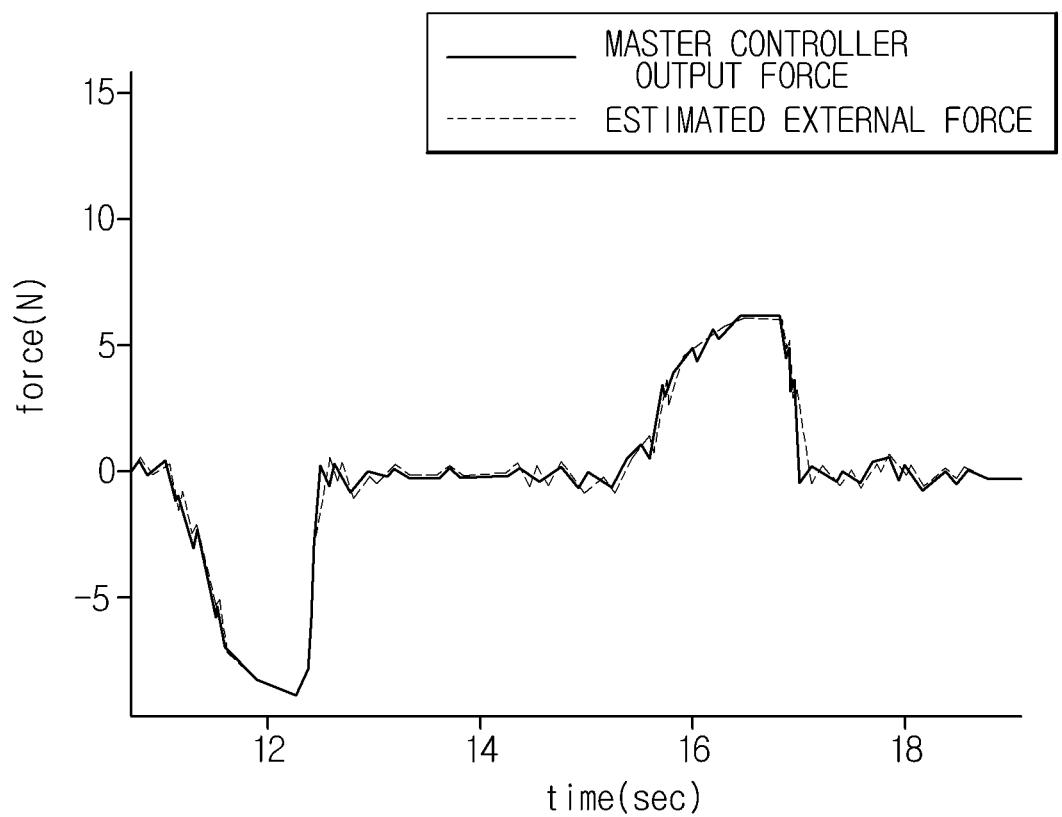
FIG. 10 is a graph representing test results regarding relations between master controller output force to a DOF in the y-axis direction and estimated external force.
Figure 11:
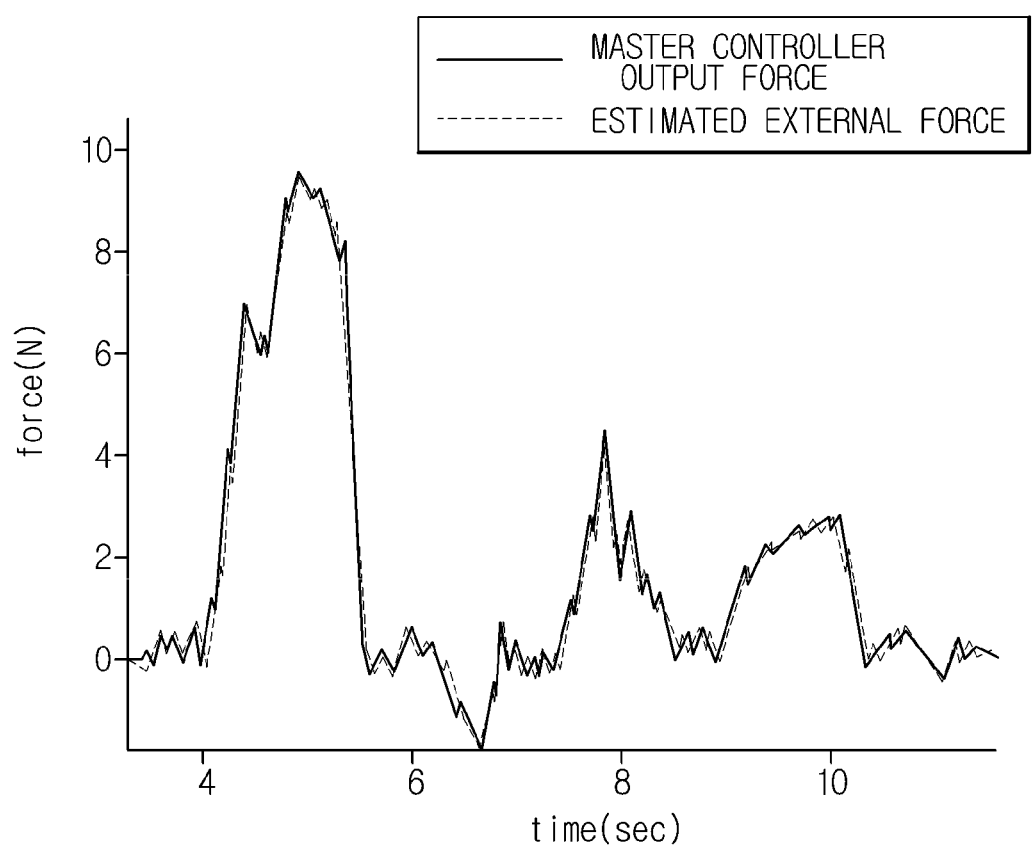
FIG. 11 is a graph representing test results regarding relations between master controller output force to a DOF in the z-axis direction and estimated external force.

FIGS. 9, 10, and 11 are graphs verifying performance of the master external estimation force of the surgical robot system in a static state.

On the assumption that the surgical robot system is in a static state (a uniform motion state or a stoppage state, e.g., a minimum acceleration state), the performance of the master external estimation force may be verified by comparing the force provided from the master controller 160 to the handles 120L and 120R with estimated external force applied to the handles 120L and 120R.

FIGS. 9, 10 and 11 represents force to a DOF in the x-axis direction, the y-axis direction, and the z-axis direction, respectively.

As shown in FIGS. 9, 10, and 11, the force provided from the master controller 160 to the handles 120L and 120R (solid line) and estimated external force applied to the handles 120L and 120R (dotted line) generally coincide with each other.

The position detection unit 122 is provided at each joint of the handles 120L and 120R, and detects the position of each joint, e.g., a joint angle. The position detection unit 122 may be, for example, a position sensor. The position sensor may employ a potentiometer or an encoder, but is not limited thereto. The position of each joint of the handles 120L and 120R, detected through the position detection unit 122, may be provided to the master external estimation unit 126, the control signal generation unit 140, and the position/velocity error compensation unit 150.

The velocity detection unit 124 is provided at each joint of the handles 120L and 120R, and detects the velocity of each joint. The velocity detection unit 124 may be, for example, a velocity sensor. The velocity of each joint of the handles 120L and 120R, detected through the velocity detection unit 124, may be provided to the master external estimation unit 126, the control signal generation unit 140, and the position/velocity error compensation unit 150.

Although FIG. 4 illustrates the master device 100 as including both the position detection units 122 and the velocity detection units 124, the velocity detection units 124 may be omitted as needed. If the velocity detection units 124 are omitted, velocity signals may be acquired by differentiating position signals detected by the position detection units 122. If the velocity detection units 124 are omitted, a velocity calculation unit (not shown) to calculate velocity signals by differentiating position signals detected by the position detection units 122 may be provided in the master device 100.

The control signal generation unit 140 generates a target position and a target velocity which each joint of the surgical tools 212 and 214 of the slave device 200 will follow using the position and velocity of each joint of the handles 120L and 120R detected through the position detection unit 122 and the velocity detection unit 124.

Hereinafter, the target position and target velocity generated through the control signal generation unit 140 of the master device 100 will be referred to as a first motion control signal. That is, the first motion control signal may be understood as being a signal of motion of the handles 120L and 120R which the surgical tools 212 and 214 will follow. The first motion control signal generated through the control signal generation unit 140 may be provided to the scaling unit 135.

The scaling unit 135 scales estimated external force multiplied by a positive gain through the force compensation unit 130, e.g., a second force control signal, by a desired (or alternatively, a predetermined) reduction ratio. At this time, the scaling unit 135 may perform scaling by applying a force scaling factor to the second force control signal. Here, the force scaling factor may be defined as '1/m' (here, m being a natural number), and be configured so as not to be changed or to be changed by the operator. When the force scaling factor is applied to the second force control signal generated through the force compensation unit 130, the operator may adjust a ratio between force applied to the handles 120L and 120R by the operator and force which will be transmitted to the surgical tools 212 and 214.

Further, the scaling unit 135 of the master device 100 may scale the first motion control signal output through the control signal generation unit 140 by a predetermined reduction ratio. For this purpose, the scaling unit 135 may apply motion scaling factors respectively to the target position and target velocity of the first motion control signal. Here, the motion scaling factors may be defined as '1/n' (here, n being a natural number), and be configured so as not to be changed or to be changed by the operator.

Further, the motion scaling factor applied to the target position and the motion scaling factor applied to the target velocity may have the same value or different values. When the motion scaling factors are applied to the first motion control signal generated through the control signal generation unit 140, a ratio between motion of the handles 120L and 120R and motion of the surgical tools 212 and 214 may be adjusted.

The scaled second force control signal and scaled first motion control signal output from the scaling unit 135 may be provided to the master controller 160.

The receive unit 195 is operated while pairing with the transmission unit 290 of the slave device 200. The receive unit 195 may receive image data and the target position and target velocity which each joint of the handles 120L and 120R will follow, from the slave device 200. The target position and target velocity which each joint of the handles 120L and 120R will follow may be values scaled by a predetermined enlargement ratio, output through the scaling unit 245 of the slave device 200.

The position/velocity error compensation unit 150 compares the current position and velocity of each joint of the handles 120L and 120R detected through the position detection unit 122 and the velocity detection unit 124 of the master device 100 with the target position and velocity of each joint of the handles 120L and 120R, received by the receive unit 195, and generates a control signal compensating for differences therebetween.

Hereinafter, the control signal generated through the position/velocity error compensation unit 150 of the master device 100 will be referred to as a first compensation control signal. The generated first compensation control signal may be understood as being a signal to control motion of the handles 120L and 120R so as to follow the motion of the surgical tools 212 and 214. The first compensation control signal generated through the position/velocity error compensation unit 150 may be provided to the master controller 160.

The master controller 160 provides control signals to the drive unit 170 provided at each joint of the handles 120L and 120R. Concretely, the master controller 160 may provide the first force control signal provided from the force compensation unit 130 and the first compensation control signal provided from the position/velocity error compensation unit 150 to the drive unit 170.

Further, the master controller 160 transmits data to the slave device 200 through the transmission unit 190. Concretely, the master controller 160 may transmit the second force control signal and the first motion control signal, scaled by the reduction ratios through the scaling unit 135, to the slave device 200.

Further, the master controller 160 may perform image processing of image data received through the receive unit 195. Image processing may include enlargement, reduction, movement, rotation, editing, and filtering of an acquired image, but is not limited thereto. However, image processing is not always performed by the master controller 160.

The drive unit 170 may be provided at each joint of the handles 120L and 120R. The drive unit 170 may be driven according to the scaled first force control signal and the scaled first compensation control signal provided from the master controller 160 and move or rotate each joint of the handles 120L and 120R.

If a signal provided from the master controller 160 is the first force control signal, the handles 120L and 120R may be driven so as to cancel out force applied to the handles 120L and 120R by the operator. Further, if the signal provided from the master controller 160 is the first compensation control signal, the handles 120L and 120R may be driven so as to follow motion of the surgical tools 212 and 214.

The display unit 180 may display image data.

The transmission unit 190 is operated while pairing with the receive unit 295 of the slave device 200. The transmission unit 190 may transmit data provided from the master controller 160, e.g., the second force control signal and the first motion control signal, scaled through the scaling unit 135, to the receive unit 295 of the slave device 200.

Further, with reference to FIG. 4, the slave device 200 includes position detection units 222, velocity detection units 224, an image acquisition unit 230, a conversion unit 240, a scaling unit 245, a position/velocity error compensation unit 250, a slave controller 260, drive units 270, the transmission unit 290, and the receive unit 295.

The position detection unit 222 is provided at each joint of the surgical tools 212 and 214, and detects the position of each joint, e.g., a joint angle. In this embodiment, the position detection unit 222 may be, for example, a position sensor. The position sensor may employ a potentiometer or an encoder, but is not limited thereto. The position of each joint of the surgical tools 212 and 214, detected through the position detection unit 222, may be provided to the conversion unit 240 and the position/velocity error compensation unit 250.

The velocity detection unit 224 is provided at each joint of the surgical tools 212 and 214, and detects the velocity of each joint. The velocity detection unit 224 may be, for example, a velocity sensor. The velocity of each joint of the surgical tools 212 and 214, detected through the velocity detection unit 224, may be provided to the conversion unit 240 and the position/velocity error compensation unit 250.

Although FIG. 4 illustrates the slave device 200 as including both the position detection units 222 and the velocity detection units 224, the velocity detection units 224 may be omitted as needed. If the velocity detection units 224 are omitted, velocity signals may be acquired by differentiating position signals detected by the position detection units 222. If the velocity detection units 224 are omitted, a velocity calculation unit (not shown) to calculate velocity signals by differentiating position signals detected by the position detection units 222 may be provided on the slave device 200.

The conversion unit 240 converts the position and velocity of each joint of the surgical tools 212 and 214, detected through the position detection unit 222 and the velocity detection unit 224, into a target position and a target velocity which each joint of the handles 120L and 120R of the master device 100 will follow.

The target position and target velocity generated through the conversion unit 240 of the slave device 200 will be referred to as a second motion control signal. That is, the second motion control signal may be understood as being a signal of motion of the surgical tools 212 and 214 which the handles 120L and 120R will follow. The second motion control signal generated through the conversion unit 240 may be provided to the scaling unit 245.

The scaling unit 245 may scale the second motion control signal output through the conversion unit 240 by a desired (or alternatively, a predetermined) enlargement ratio. For this purpose, the scaling unit 245 may apply motion scaling factors respectively to the target position and target velocity of the second motion control signal output from the conversion unit 240. Here, the motion scaling factors applied by the scaling unit 245 of the slave device 200 may be defined as the reciprocal numbers (n) of the motion scaling factors applied by the scaling unit 135 of the master device 100. The second motion control signal scaled by the enlargement ratio through the scaling unit 245 may be provided to the slave controller 260.

The receive unit 295 is operated while pairing with the transmission unit 190 of the master device 100. The receive unit 295 may receive data from the master device 100. Concretely, the receive unit 295 may receive the second force control signal and the first motion control signal, scaled by the reduction ratios from the scaling unit 135. The scaled second force control signal may be provided to the slave controller 260, and the scaled first motion control signal may be provided to the position/velocity error compensation unit 250.

The position/velocity error compensation unit 250 compares the current position and velocity of each joint of the surgical tools 212 and 214 detected through the position detection unit 222 and the velocity detection unit 224 of the slave device 200 with the target position and target velocity of the scaled first motion control signal, and generates a control signal compensating for differences therebetween.

The control signal generated through the position/velocity error compensation unit 250 of the slave device 200 will be referred to as a second compensation control signal. The generated second compensation control signal may be understood as being a signal to control motion of the surgical tools 212 and 214 so as to follow the motion of the handles 120L and 120R. The generated second compensation control signal may be provided to the slave controller 260.

The image acquisition unit 230 may acquire image data. For example, the image acquisition unit 230 may acquire image data of a surgical site by photographing the inside of the abdominal cavity of a patient. The image acquisition unit 230 may be the endoscope 216 shown in FIG. 3. The image data acquired through the image acquisition unit 230 may be provided to the slave controller 260.

The slave controller 260 may provide control signals to the drive unit 270 provided at each joint of the surgical tools 212 and 214. Concretely, the slave controller 260 may provide the scaled second force control signal, provided from the master device 100 through the reception unit 295, and the second compensation control signal, provided from the position/velocity error compensation unit 250, to the drive unit 270.

Further, the slave controller 260 provides data to the transmission unit 290 for the transmission unit 290 to transmit to the master device 100. The data may be the second motion control signal scaled by the enlargement ratio through the scaling unit 245, but is not limited thereto.

Further, the slaver controller 260 may perform image processing of the image data acquired through the image acquisition unit 230. The image processing may include enlargement, reduction, movement, rotation, editing, and filtering of an acquired image, but is not limited thereto.

The drive unit 270 may be provided at each joint of the surgical tools 212 and 214. Further, the drive unit 270 is driven according to the scaled second force control signal and second compensation control signal provided from the slave controller 260 and moves or rotates each joint of the surgical tools 212 and 214.

If a signal provided from the slave controller 260 is the scaled second force control signal, the surgical tools 212 and 214 may be driven so as to follow force applied to the handles 120L and 120R by the operator. Further, if the signal provided from the slave controller 260 is the second compensation control signal, the surgical tools 212 and 214 may be driven so as to follow motion of the handles 120L and 120R.

The transmission unit 290 is operated while pairing with the receive unit 195 of the master device 100. The transmission unit 290 may transmit the second motion control signal scaled by the enlargement ratio through the scaling unit 245 and the image data acquired through the image acquisition unit 230 to the master device 100.

A configuration of the surgical robot system in accordance with example embodiments has been described with reference to FIG. 4.

Although FIG. 4 illustrates, the master device 100 and the slave device 200 as respectively including the separate scaling units 135 and 245, example embodiments are not limited thereto. That is, both a scaling unit to perform scaling by a reduction ratio and a scaling unit to perform scaling by an enlargement ratio may be included in either the master device 100 and/or the slave device 200.

Figure 5:
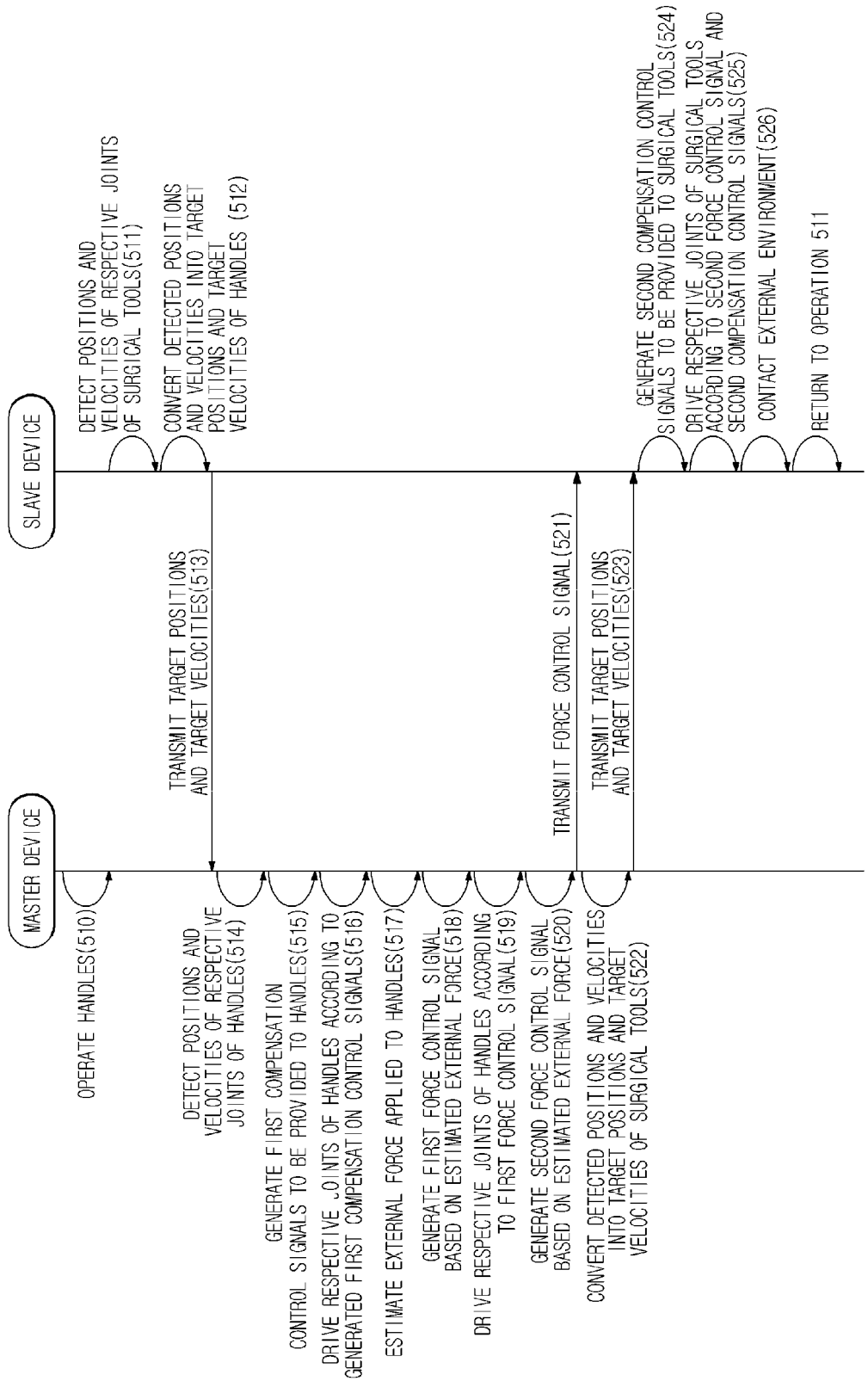
FIG. 5 is a conceptual diagram sequentially illustrating a control method of the surgical robot system.

FIG. 5 is a conceptual diagram sequentially illustrating a control method of the surgical robot system in accordance with an example embodiment.

Referring to FIGS. 1 to 5, when the handles 120L and 120R of the master device 100 are operated by an operator (Operation 510), the position detection units 122 and the velocity detection units 124 of the master device 100 detect the positions and velocities of the respective joints of the operated handles 120L and 120R (Operation 514).

Further, the position detection units 222 and the velocity detection units 224 of the slave device 200 detect the positions and velocities of the respective joints of the surgical tools 212 and 214 (Operation 511). The detected positions and velocities of the respective joints of the surgical tools 212 and 214 are converted into second motion control signals including target positions and target velocities of the respective joints (Operation 512). Thereafter, the slave device 200 transmits the second motion control signals to the master device 100 (Operation 513). Although not shown in FIG. 5, the control method may include scaling the second motion control signals by a predetermined enlargement ratio, prior to transmission of the second motion control signals to the master device 100.

The position/velocity error compensation unit 150 of the master device 100 compares the positions and velocities detected through Operation 514 with the target positions and velocities of the respective joints of the handles 120L and 120R included in the second motion control signals transmitted from the slave device 200, and generates first compensation control signals compensating for differences therebetween (Operation 515).

Thereafter, the master controller 160 provides the first compensation control signals generated through the position/velocity error compensation unit 150 to the drive units 170 to move and rotate the respective joints of the handles 120L and 120R so that the handles 120L and 120R are operated to follow motion of the surgical tools 212 and 214 (Operation 516).

Thereafter, the master external force estimation unit 126 of the master device 100 estimates external force applied to the handles 120L and 120R by the operator using driving force according to the positions and velocities of the respective joints of the handles 120L and 120R detected through Operation 514 and the first compensation control signals generated in operation 515 by the position/velocity error compensation unit 150 (Operation 517). The detail process of estimating external force through the master external force estimation unit 126 has been described above, and a description thereof will thus be omitted.

Thereafter, a first force control signal, used to control the handles 120L and 120R, is generated based on the external force estimated through Operation 517 (Operation 518). Here, the first force control signal may be generated by multiplying the estimated external force by a negative gain. Here, the gain may have a value of less than 1, but is not limited thereto.

Thereafter, the master controller 160 provides the first force control signal generated through Operation 518 to the drive units 170 to move and rotate the respective joints of the handles 120L and 120R so that the handles 120L and 120R are operated to cancel out the external force applied by the operator (Operation 519). Thereby, the operator may sense force applied to the external environment by the surgical tools 212 and 214, e.g., force applied from the external environment to the surgical tools 212 and 214.

Further, a second force control signal, which will be provided to the surgical tools 212 and 214 of the slave device 200, is generated based on the external force estimated through Operation 517 (Operation 520). Here, the second force control signal may be generated by multiplying the estimated external force by a positive gain. Here, the gain may have a value of less than 1, but is not limited thereto.

Thereafter, the generated second force control signal is transmitted to the slave device 200 (Operation 521). Although not shown in FIG. 5, the control method may further include scaling of the second force control signal by a desired (or alternatively, a predetermined) reduction ratio, prior to transmission of the second force control signal to the slave device 200.

Further, the control signal generation unit 140 of the master device 100 generates first motion control signals including target positions and target velocities of respective joints of the surgical tools 212 and 214 using the positions and velocities of the respective joints of the handles 120L and 120R detected through Operation 514 (Operation 522), and transmits the generated first motion control signals to the slave device 200 (Operation 523). Although not shown in FIG. 5, the control method may further include scaling of the first motion control signals by a desired (or alternatively, a predetermined) reduction ratio, prior to transmission of the first motion control signals to the slave device 200.

Thereafter, the position/velocity error compensation unit 250 of the slave device 200 compares the positions and velocities of the surgical tools 212 and 214 detected through Operation 511 with the target positions and velocities of the respective joints of the surgical tools 212 and 214 included in the received first motion control signals, and generates second compensation control signals compensating for differences therebetween (Operation 524).

Thereafter, the slave controller 260 provides the second force control signals transmitted from the master device 100 and the second compensation control signals generated through the position/velocity error compensation unit 150 to the drive units 270 to move and rotate the respective joints of the surgical tools 212 and 214 (Operation 525). The generated second compensation control signals may be understood as being motion control signals to control the motion of the surgical tools 212 and 214 so as to follow motion of the handles 120L and 120R. If the received signal is the second force control signal, the surgical tools 212 and 214 may be operated to follow external force applied to the handles 120L and 120R by the operator, and if the received signal is the second compensation control signal, the surgical tools 212 and 214 may be operated to follow motion of the handles 120L and 120R.

If the surgical tools 212 and 214 of the slave device 200 contact the external environment (for example, the inside or organs of a human body), the control method returns to Operation 511, and then the subsequent Operations are sequentially carried out. Thereby, force applied to the external environment by the surgical tools 212 and 214, e.g., force applied from the external environment to the surgical tools 212 and 214, may be estimated, and cause the handles 120L and 120R to generate the estimated force so that the operator may sense external force applied to the surgical tools 212 and 214.

In the above-described embodiments, some of the elements of the master device 100 and the slave device 200 may be implemented as a 'module'. Here, the 'module' means software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more CPUs in a device.

Some of the example embodiments may be implemented through a medium including computer readable codes/instructions to control at least one processing element of the above-described embodiment, for example, a computer readable medium. Such a medium may correspond to a medium/media which may store and/or transmit the computer readable codes.

The computer readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer readable medium. Since the medium may be a distributed network, the computer readable code may be stored, transmitted and executed in a distributed manner. Further, for example, the processing element may include a processor or a computer processor, and be distributed and/or included in one device.

Although a few example embodiments have been shown and described, it would be appreciated by those skilled in the art that changes may be made in these embodiments without departing from the principles and spirit of the presented example embodiments, the scope of which is defined in the claims and their equivalents. For example, while certain operations have been described as being performed by the controller associated with the master device 100 or the slave device 200, one of ordinary skill in the art will appreciate that the operations may be divided between the controllers in various manners. For example, the operations discussed as being performed by the controllers may be segmented between controllers of a plurality of master devices 100 and a plurality of slave devices 100. Further, various operations discussed as being performed by the controller the master device 100 may be performed by the controller of the slave device 200, and vice versa.

Additionally, while example embodiments have been described with relation to a surgical robot, one of ordinary skill in the art will appreciate that the example embodiments may be applied to extend the working space of various other robot systems. For example, robotic systems for use various manufacturing industries. Likewise, in such embodiments, the surgical tools described herein as being attached to the guide tube may be replaced with various tools other than surgical tools. For example, tools utilized in various manufacturing industries. Examples of various tools may include hand tools (e.g., a hammer, anvil, chisel, etc.) and electronic tools (e.g., a welder, torch, etc.).

What is claimed is:

1. A surgical robot system comprising:
    a slave device provided with surgical tools; and
    a master device configured to remotely control motion of the surgical tools, the master device including,
        a handle configured to control the motion of the surgical tools,
        a master external force estimation unit configured to estimate an external force applied to the handle,
        a force compensator configured to generate a first force control signal that cancels out the estimated external force, and
        a master controller configured to control moving and rotating of respective joints of the handle in such a way that the external force applied to the handle is cancelled out using the generated first force control signal.

2. The surgical robot system according to claim 1, wherein the master device further comprises:
    a position detection configured to detect positions of the respective joints of the handle;
    a velocity detection configured to detect velocities of the respective joints of the handle; and
    a control signal generator configured to generate target positions and target velocities of the surgical tools using the detected positions and velocities of the respective joints of the handle.

3. The surgical robot system according to claim 2, wherein the master device further comprises:
    a position/velocity error compensator configured to,
        compare current positions and current velocities of the surgical tools transmitted from the slave device with the target positions and target velocities of the surgical tools generated through the control signal generator, and
        generate compensation control signals that compensate for differences therebetween.

4. The surgical robot system according to claim 3, wherein the master external force estimator is configured to estimate external force applied to the handle using the detected positions and velocities of the respective joints of the handle and the compensation control signals.

5. The surgical robot system according to claim 3, wherein the master device further comprises:
    a scaler configured to scale the target positions and target velocities of the surgical tools, generated through the control signal generator, by a reduction ratio.

6. The surgical robot system according to claim 5, wherein:
    the force compensator is configured to generate a second force control signal by multiplying the external force estimated through the master external force estimation unit by a positive gain; and
    the scaler is configured to scale the generated second force control signal by a reduction ratio.

7. The surgical robot system according to claim 6, wherein the gain has a value of less than 1.

8. The surgical robot system according to claim 1, wherein the force compensator is configured to generate the first force control signal by multiplying the external force estimated through the master external force estimator by a negative gain.

9. The surgical robot system according to claim 8, wherein the gain has an absolute value of less than 1.

10. A control method of a surgical robot system, the control method comprising:

detecting positions and velocities of respective joints of a handle;

generating target positions and target velocities of surgical tools using the detected positions and velocities of the respective joints of the handle;

generating compensation control signals that indicate an amount of compensation for differences between the target positions and target velocities of the surgical tools and current positions and current velocities of the surgical tools, through comparison therebetween;

estimating external force applied to the handles using the generated compensation control signals and the detected positions and velocities of the respective joints of the handle;

generating a first force control signal indicating an amount of force to apply to cancel out the external force; and driving the respective joints of the handle in such a way that the external force applied to the handles is cancelled out using the generated first force control signal.

11. The control method according to claim 10, wherein the generating the first force control signal is performed by multiplying the estimated external force by a negative gain.

12. The control method according to claim 11, wherein the gain has an absolute value of less than 1.

13. The control method according to claim 10, wherein the generating the first force control signal comprises:

generating a second force control signal configured to control the surgical tools such that the surgical tools are operated at a force that is commensurate to the force applied to the handle.

14. The control method according to claim 13, wherein the generating the second force control signal is performed by multiplying the estimated external force by a positive gain.

15. The control method according to claim 14, wherein the gain has a value of less than 1.

16. The control method according to claim 13, further comprising, after the generating the second force control signal:

scaling the generated second force control signal by a reduction ratio; and transmitting the scaled second force control signal to a slave device that controls the force at which the surgical tools are operated.

17. The control method according to claim 10, further comprising, after the generating of the target positions and target velocities of the surgical tools:

scaling the generated target positions and target velocities by a reduction ratio; and transmitting the scaled target positions and target velocities to a slave device that controls a force at which the surgical tools are operated.

18. A master device configured to control surgical tools of a slave device, the master device comprising:

an input device configured to receive input from an operator, the input indicating a desired target position and velocity of the surgical tools;

a driver configured to move the input device; and a controller configured to, receive, via a receiver, detected forces applied to joints of the surgical tools from the slave device, instruct the driver to move the input device with a feedback force that is commensurate with the detected forces applied to the joints of the surgical tools, estimate the input to the input device by the operator while the driver is providing the feedback force to the input device, instruct the driver to move the input device with an adjustment force that counteracts the input received while providing the feedback force such that the operator can sense the forces applied to the joints of the surgical tools, and transmit, via a transmitter, the desired target position and velocity of the surgical tools to the slave device.

19. The master device of claim 18, wherein the input from the operator is conveyed to the input device by moving joints included in the input unit, and the controller estimates the input using detection units that are configured to detect a position and velocity of the joints included in the input unit.

* * * * *